United States Patent [19]
Morgan

[11] Patent Number: 5,940,892
[45] Date of Patent: Aug. 24, 1999

[54] EYE PROTECTION DEVICE CONSTRUCTED FROM AN ELONGATED STRIP OF TRANSLUCENT MATERIAL

[75] Inventor: David H. Morgan, Barrington, Ill.

[73] Assignee: Morgan Evans Industries, Inc., Barrington, Ill.

[21] Appl. No.: 09/119,988

[22] Filed: Jul. 21, 1998

[51] Int. Cl.⁶ .................................................. A61F 9/02
[52] U.S. Cl. .......................... 2/430; 2/428; 2/454; 351/44
[58] Field of Search .............................. 2/426, 428, 439, 2/445, 446, 452, 454, 431, 430, 432, 12; 351/153, 44, 41

[56] References Cited

U.S. PATENT DOCUMENTS

| | | | |
|---|---|---|---|
| 2,179,286 | 1/1939 | English | 2/12 |
| 2,377,645 | 6/1945 | Peffer | 2/12 |
| 2,568,316 | 9/1951 | Brown | 2/428 |
| 2,792,744 | 5/1957 | Hirch | 351/41 |
| 2,907,041 | 10/1959 | Finn | 2/432 |
| 3,787,113 | 1/1974 | Shedrow | 351/43 |
| 4,217,037 | 8/1980 | Lemelson | 351/44 |
| 4,520,510 | 6/1985 | Daigle | 2/452 |
| 4,729,650 | 3/1988 | Jennings | 351/47 |
| 4,853,974 | 8/1989 | Olim | 2/9 |
| 4,898,460 | 2/1990 | Magninat et al. | 351/114 |
| 5,214,804 | 6/1993 | Carey et al. | 2/206 |
| 5,268,710 | 12/1993 | Anstey | 351/121 |
| 5,428,407 | 6/1995 | Sheffield | 351/58 |
| 5,537,687 | 7/1996 | Garza | 2/9 |
| 5,608,470 | 3/1997 | Sheffield | 351/47 |
| 5,636,388 | 6/1997 | Hodges | 2/443 |
| 5,713,078 | 2/1998 | DeAngelis | 2/209 |
| 5,818,569 | 10/1998 | Berent | 351/156 |

*Primary Examiner*—John J. Calvert
*Assistant Examiner*—Tejash D Patel
*Attorney, Agent, or Firm*—Jon Carl Gealow

[57] ABSTRACT

An eye protection device is formed of an elongated strip of translucent material. The length of the elongated strip of translucent material is such that it will encircle the wearer's head, with strap-like portions overlapping at the back of a wearer's head and being secured to each other. The elongated strip of translucent material is formed with two enlarged eye protection portions spaced apart by a nose bridging portion, with strap-like portions extend from each of the enlarged eye protection portions. A cushioning material encircles the eye protection area and nose bridging portions, somewhat in the shape of a figure eight. Complementary securing means are applied adjacent the ends of the strap-like portions so as to engage each other at the back of a wearer's head to retain the eye protection device over a wearer's eyes. For the comfort of a user, cushioning pads are provided on the strap-like portions in the regions where the strap-like portions pass behind a users ears.

26 Claims, 3 Drawing Sheets

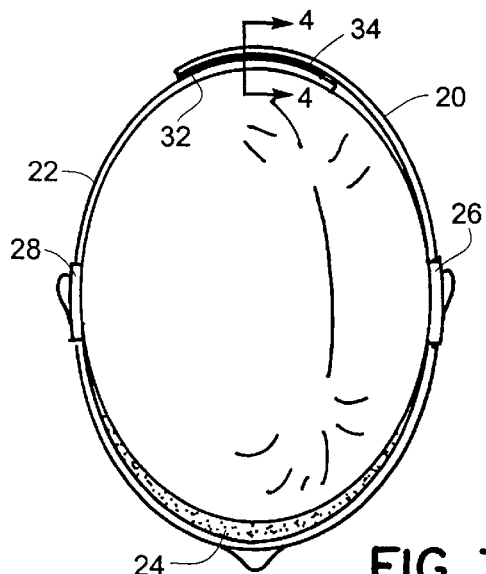
FIG. 3
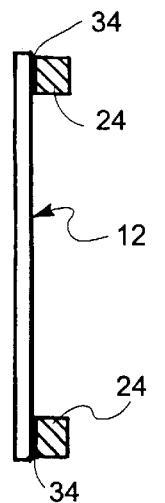
FIG. 5
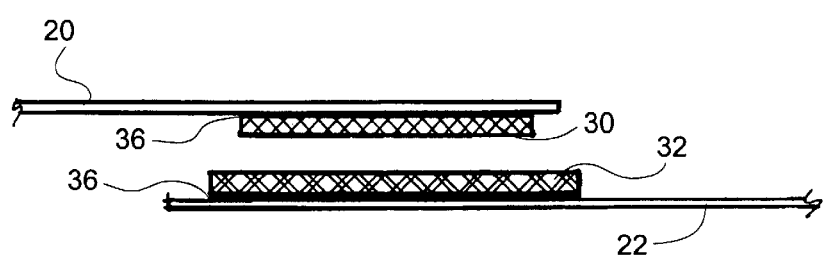
FIG. 4
FIG. 6
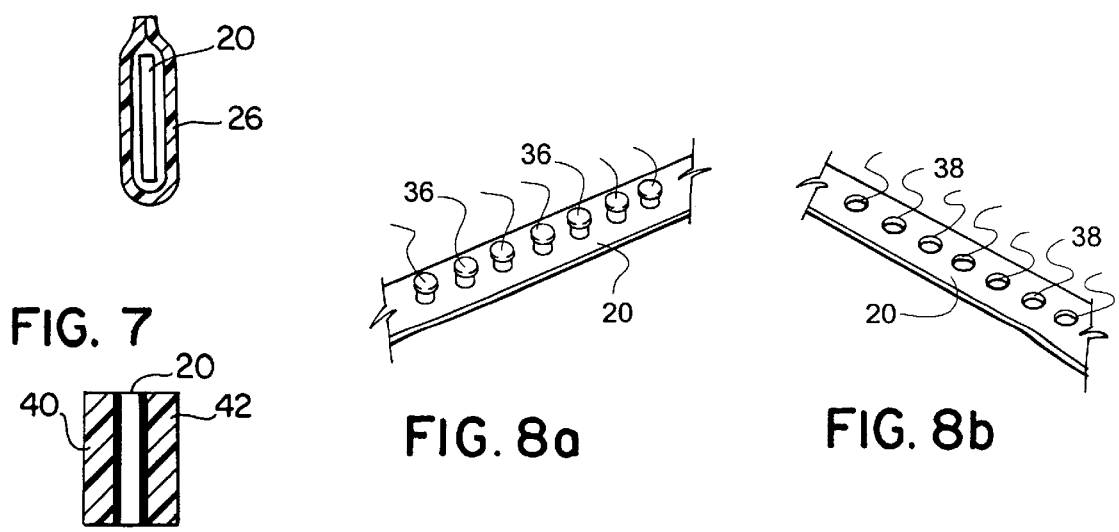
FIG. 7
FIG. 8a
FIG. 8b

EYE PROTECTION DEVICE CONSTRUCTED FROM AN ELONGATED STRIP OF TRANSLUCENT MATERIAL

FIELD OF THE INVENTION

The present invention relates to a device for protecting the eyes of a wearer from contact with materials which would otherwise be directed into contact with a wearer's eyes. More particularly it relates to an eye protection device which is of such unique and inexpensive construction that it is economically feasible to use it only once, and then disposed of it.

BACKGROUND OF THE INVENTION

Various types of eye protection devices have been provided in the past to protect a wearer's eyes from contact with materials which would otherwise be directed into contact with a wearer's eyes. The material and labor costs of most, if not all. such prior eye protection devices are such that in most cases the device is used on more than one occasion. Such eye protection devices may require cleaning between uses, particularly if a material is deposited on the surface through which a viewer must see. Further, in certain applications, such as those in health care facilities, it may be necessary to not only clean, but also sterilize the eye protection devices between uses. Such sterilizing, usually in autoclaves, is quite costly. Further, pronouncements by federal and state agencies have become increasingly critical of autoclaves and their use. For these reasons, health care facilities have been increasing their use of throwaway devices of various types, so as to avoid in-house sterilizing of reusable devices and materials. Further, so called "streetfront" health clinics, which are under severe spending constraints are in need of a less expensive alternative for providing eye protection for all of their personnel.

A further example of the desirability of disposable eye shields is presented by dental offices. The conventional eye shields used in dental offices must be sterilized between uses. As previously set forth, sterilization is a costly and time consuming operation, which usually shortens the useful life of conventional eye shields. Not only could the professionals in a dental office use a disposable eye shield, but also the patients. With the use of a disposable eye shield, the patient's eyes would be protected from any materials splattered as a result of the dental procedures being performed.

Accordingly, it would be advantageous to provide an eye protection device, the materials and labor costs of assembling being such that the device will be considered disposable after a single use. It would also be advantageous to provide such a device in a form which is adaptable to be worn without regard to size, that is, it can be adjusted to fit most if not all potential wearers. It would also be advantageous to provide an eye protection device which would meet federal and state agency requirements relating to blood pathogens and the need for hospital employees to wear eye protective devices.

Such disposal eye protection devices would also be found useful by those involved in spraying various types of materials. For instance, they would provide protection to a person applying aerated disinfectants and cleaning compounds in an ordinary household setting. Gardeners would find them useful when applying aerated pest sprays, and painters would find them useful when spraying paint, or painting overhead with any type of applicator. Artists using air brushes to apply paint and hair stylist applying hair care products using an aerosol container would also find a disposable eye protection device useful. A low cost disposable eye protection device could be provided along with an aerosol product, or it could be marketed in conjunction with aerosol products.

A low cost disposable eye protection device could also be distributed as a novelty or promotional item. Tinted translucent material could be used in the disposable eye protection device, either to color the users vision or as an inexpensive type of sunglass. Depending on the type of translucent material used, the eye protection devices could be used as sunglasses in non-contact or contact sports, and by beach-goers, where if the translucent material is scratched by the sand, the eye protection device would merely be disposed of, without the concern for damage one would have with more expensive sunglasses. Further, advertising legends such as brand names or logos could be applied to the eye protection devices, distributed as advertising handouts.

SUMMARY OF THE INVENTION

It is an object of this invention to provide an eye protection device which may be assembled at reduced materials and labor cost. It is a further object of this invention to provide an eye protection device which is adapted to be readily worn by most if not all wearers. It is another object of this invention to provide an eye protection device which is readily assembled from a minimum number of parts. It is still another object of this invention to provide a low cost throwaway eye protector for use in environments that may contain impurities which could cause damage to unprotected eyes.

An eye protection device in accordance with this invention is formed from a single elongated sheet of translucent material which is cut to form two enlarged eye protection areas separated by a narrower nose bridging portion, and with a narrow strap-like portion extending from each of the enlarged eye protection areas. A cushioning material is secured around the outer periphery of each of the enlarged eye protection areas and the nose bridging portion. Complementary securing devices are provided on the strap-like portions, such that when the enlarged eye protection areas are placed over a wearer's eyes with the cushioning material engaging the wearer's face, the strap-like portions may encircle the wearer's head and be secure to each other at the back of the wearer's head. The sections of the strap-like portions which are positioned behind a wearer's ears are provided with a cushioning material to provide additional comfort to the wearer's.

BRIEF DESCRIPTION OF THE DRAWINGS

FIG. 3 is top view of a person wearing an eye protection device in accordance with this invention as shown in FIG. 1;

FIG. 4 is a cross-sectional view taken along the line 4—4 in FIG. 3;

FIG. 5 is a cross-sectional view taken along the line 5—5 in FIG. 2:

FIG. 6 is a cross-sectional view taken along the line 6—6 in FIG. 2;

FIG. 7 is a cross-sectional view, similar to FIG. 6, of an alternate embodiment of an ear cushioning pad for an eye protection device in accordance with this invention;

FIGS. 8a and 8b are perspective views of the strap-like portions of an eye protection device in accordance with this invention, as shown in FIG. 1, showing an alternate embodiment of the complementary engaging devices on the strap-like portions of the elongated flexible translucent material;

FIG. 9b is a perspective view of the alternate embodiment of the complementary engaging device on one of the strap-like portions of the elongated flexible translucent material as shown in FIG. 9a.

DETAILED DESCRIPTION OF THE PREFERRED EMBODIMENT

Figure 1:
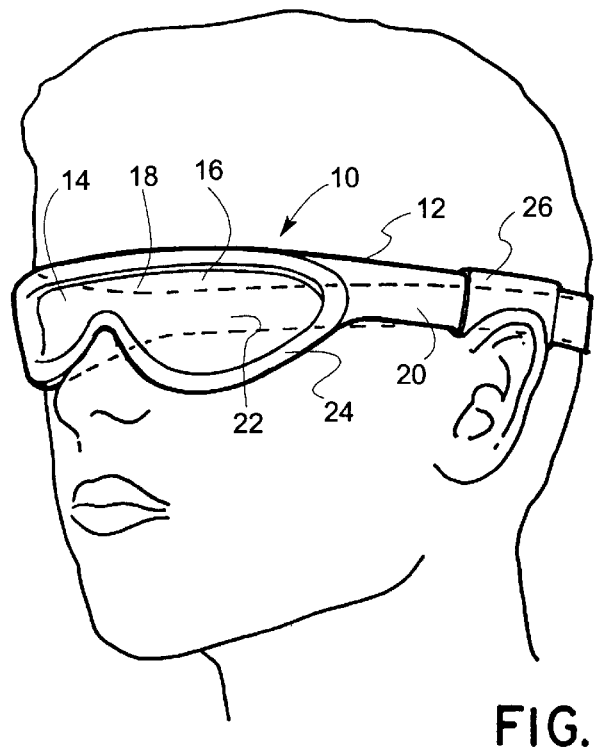
FIG. 1 is a perspective view showing a person wearing an eye protection device in accordance with this invention.

Referring to FIG. 1, a person is shown wearing an eye protection device 10 in accordance with one embodiment of this invention. As shown is FIG. 1, the eye protection device 10 includes an elongated flexible translucent member 12 which encircles the wearer's head. The elongated translucent member 12 is shaped to provide two enlarged eye protection portions 14 and 16 separated by a nose bridging portion 18. A pair of strap-like portions 20 and 22 extend from the eye protection portions 14 and 16 respectively. The enlarged eye protection portions 14 and 16 are sufficiently close together and of adequate length to accommodate the spacing of most if not all potential wearer's eyes. When used by wearer's with closer spaced eyes, the excess enlarged eye protection portions will wrap around the side of the wearer's head.

Figure 2:
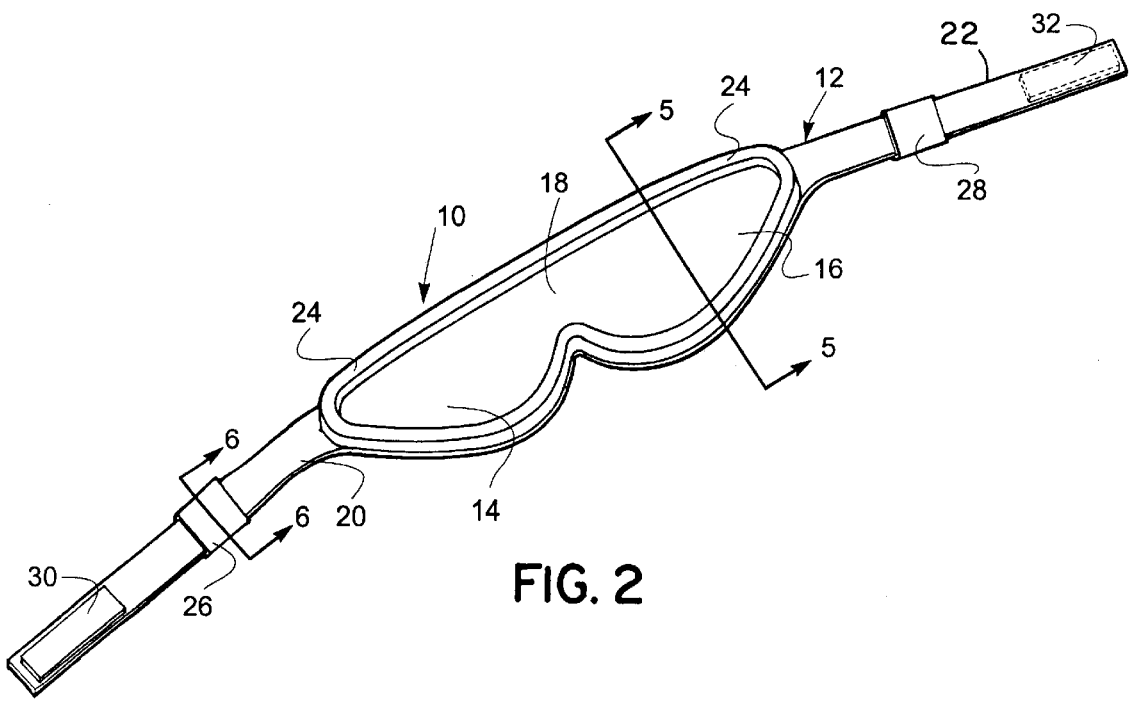
FIG. 2 is a perspective view of an eye protection device in accordance with this invention as shown in FIG. 1.

Making reference to FIG. 2 in addition to FIG. 1, a cushioning material 24 is secured to the translucent member 12, encircling the outer periphery of the eye protection portions 14 and 16 and nose bridging portion 18. Cushioning pads 26 and 28 are also provided on the strap-like portions 20 and 22 respectively, to provide comfort for the wearer where the straps pass behind the ear of the wearer as shown in FIG. 1. The free ends of the strap-like portions 20 and 22 are provided with complementary engaging devices 30 and 32 respectively, which may be engaged with each other after the eye protection portions 14 and 16 are placed over the eyes of a wearer, and the strap-like portions are brought around the sides and into an overlapping position at the back of the head of a wearer as shown in FIG. 3.

Many translucent materials may be used in forming the translucent member 12. Suitable translucent materials include polyesters, polycarbonates, which are shock resistant, ABS (acrylonitrile butadiene styrene), styrene, polyethalene, acetate, Mylar®, and Teflon®, to name a few. The particular material chosen for use will depend upon the environment in which the eye protection device is intended be used. For instance, a less expensive polyester material, which is only 0.05 mils thick, may be employed when the eye protection device is used to prevent the contact of water and other non-corrosive liquids from contacting the eyes. Typical of such applications would be for protection of peoples eyes in a dentist's office or for the protection of the eyes of painters. More generally, in so far as the liquid material impinging on the translucent material will not chemically attack the translucent material, the less expensive translucent materials should be suitable for use. It is particularly desirable to use the less expensive translucent material in applications where the eye shields may be disposed of, rather than having to sterilized them for reuse, such as by processing them in autoclaves between uses.

Depending upon the use for which the eye protection device is intended, different translucent materials may be used. For instance, to provide protection against corrosive materials, Teflon® may be used. Where hard particulate material may be directed toward a person's eyes, an impact resistant translucent material, such as a polycarbonate, would be used. In still other cases, to provide protection from excessively bright light, or to enhance vision with color correction, tinted translucent materials may be used.

Should the eye protection device be intended for use in conditions where fogging of the translucent material is likely, an anti-fog coating may be applied to the translucent material, or an anti-fog additive may be added to the material from which the elongated sheet of translucent material is formed.

The cushioning material 24 is, in a preferred embodiment, formed of strip of open cell foam approximately ½ inch thick and ¼ to ⅜ inch wide. However, closed cell foam could also be used, depending upon the intended use of the eye protectors. The cushion material 24 is secured to the elongated translucent member by an adhesive 34 as shown in FIG. 5. The adhesive material may be applied to either the elongated translucent member 12, or to the cushioning material 24. For instance, the adhesive material may be applied to the cushioning material 24, and then covered by a material which is peeled off before the cushioning material 24 is brought into contact with the translucent member 12.

While perhaps in a less expensive manner of producing the eye protector the cushioning material 24 would be of uniform thickness for a better fit with a user's face, the material could be of varying thickness. That is, thinner along the lower edge of the nose bridging portion and thicker on the bottom edges of the eye protection portions so as to engage the wearer's checks, thereby preventing air-borne materials from passing behind the translucent eye protection portions when directed upward toward the user's face. Stated in more general terms, the thickness of the cushioning material 24 would be contoured to provide compressive contact, throughout its contacting surface, with a users face.

The complementary engaging devices 30 and 32 in a preferred embodiment of this invention are pieces of hook and loop type fastening materials. For instance complementary engaging device 30 is a pad of hook material and complementary engaging device 32 is a pad of loop material. As in the case of the cushioning material 24, the complementary engaging devices 30 and 32 may be secured to the strap-like portions of the elongated flexible translucent member 12 by an adhesive 36. Again, the adhesive material may be applied to either the elongated translucent member 12, or to the complementary engaging devices 30 and 32. For instance, the adhesive material may be applied to the back of the complementary engaging devices 30 and 32, when of the hook and loop type material, and then covered by a material which is peeled off before the engaging devices 30 and 32 are brought into contact with the strap-like portions 20 and 22 of the elongated flexible translucent member 12.

In another embodiment of an aspect of this invention, the complementary engaging devices 30 and 32 may be formed from the elongated flexible translucent member as shown in FIGS. 8a and 8b. As shown in FIG. 8a, a row of projecting nibs 36 are formed in the strap-like portion 20, such as by heating the translucent material and then deforming it in a die stamping operation. Similarly, FIG. 8b shows a row of holes 38 formed in the strap-like portion 22. With this embodiment of the complementary engaging devices 30 and 32, the free ends of the strap-like portions 20 and 22 after encircling the wearer's head, are pressed against each other, and if necessary, slightly adjusted with respect to each other such that at least several of the projecting nibs 36 are received in several of the holes 38. With the elongated flexible translucent member held in tension while engaging the holes 38 and the projecting nibs 36, the tension will maintain the engagement of the holes 38 and nibs 36.

Figure 9A:
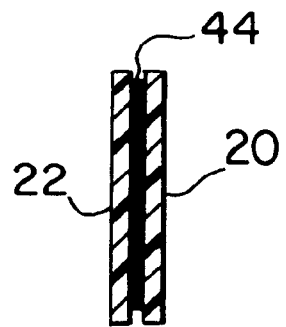
FIG. 9a is cross-sectional view of an alternate embodiment of the complementary engaging device on one of the strap-like portions of the elongated flexible translucent material.
Figure 9B:
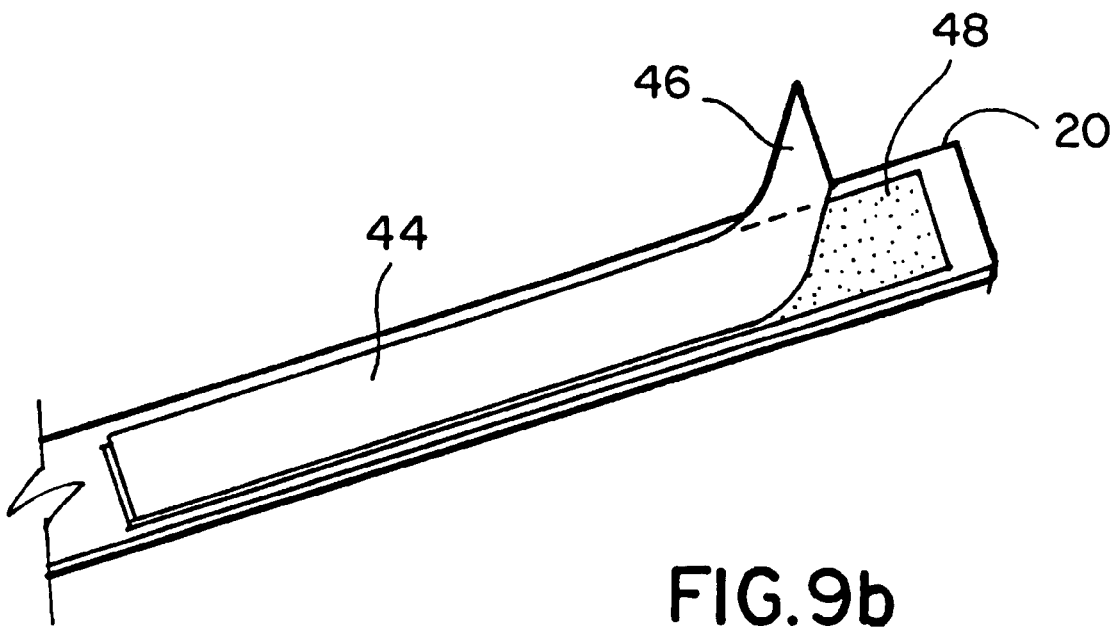

In still another embodiment of an aspect of this invention, the complementary engaging devices may be formed by an elongated piece of double faced tape 44 as shown in FIGS. 9a and 9b. The protective covering is removed from one side of the tape 44, so as to secure it to one of the strap-like portions, such as 20 as shown in FIG. 9b. When the eye protection device is about to be secured over a user's head, the second protective covering 46 is removed from the second adhesive surface 48 of the tape 44, such that it can be brought into engagement with the abutting surface of the second strap-like portion 22.

As shown in FIGS. 1–3, and 6, the ear cushioning pads 26 and 28 encircle the strap-like portions 20 and 22. The cushioning pads 26 and 28 may be formed of various cushioning materials, including open and closed cell plastic foam. As shown in FIG. 6, the cushioning pads 26 and 28 are formed as loops of cushioning material which encircles the strap-like portions 20 and 22, with the overlapping ends being secured to each other, such as by an adhesive. When formed in this way, the cushioning pads 26 and 28 may be slid along the strap-like portions 20 and 22, by a person using the eye protection device so as to properly position them with respect to their ears.

In another embodiment of an aspect of this invention as shown in FIG. 7, the ear cushioning pads may be formed by securing cushioning materials 40 and 42 to both sides of each strap-like portion 20 and 22 over a length of each strap-like portion so as to have at least a portion of the cushioning material in the correct position to cushion most wearer's ears.

While only one embodiment of the invention has been shown, with variations of certain features, it should be apparent to those skilled in the art that what has been described is considered at present to be a preferred embodiment of the eye protection device of this invention. In accordance with the Patent Statute, changes may be made in the eye protection device without actually departing from the true spirit and scope of this invention. The appended claims are intended to cover all such changes and modification which fall in the true spirit and scope of this invention.

What is claimed is:

1. A device for protection of a person's eyes comprising:
    an elongated strip of translucent material, said strip being formed with two wider eye protection portions spaced apart on adjacent sides by a narrower nose bridging portion, and with a pair of elongated strap-like portions extending from the other sides of said wider eye protection portions,
    a cushioning material surrounding the outer periphery of the two wider eye protection portions and the narrower nose bridging portion and secured to one side of said elongated strip of translucent material for engaging a person's face, and
    a pair of complementary fastening means, one of said pair of complementary fastening means being provided on each of said elongated straps, said elongated straps being secured to each other by said pair of complementary fastening means to retain said device over the eyes of a person.

2. The device for protection of a person's eyes of claim 1, wherein said cushioning material is a plastic foam.

3. The device for protection of a person's eyes of claim 2, wherein said plastic foam is of the open cell type.

4. The device for protection of a person's eyes of claim 2, wherein said plastic foam is of the closed cell type.

5. The device for protection of a person's eyes of claim 1, wherein said cushioning material is secured to said elongated strip of translucent material by an adhesive.

6. The device for protection of a person's eyes of claim 1, wherein said strip of translucent material is formed of a polyester material.

7. The device for protection of a person's eyes of claim 1, wherein said strip of translucent material is formed of Mylar.

8. The device for protection of a person's eyes of claim 1, wherein said strip of translucent material is formed of Teflon.

9. The device for protection of a person's eyes of claim 1, wherein said strip of translucent material is tinted.

10. The device for protection of a person's eyes of claim 1, wherein said cushioning material extends at varying distances from the translucent material, so as to maintain compressing contact with a persons face throughout its surface facing the person.

11. The device for protection of a person's eyes of claim 1, wherein an ear cushioning pad is provided on each of said elongated strap-like portions.

12. The device for protection of a person's eyes of claim 11, wherein said ear cushioning pads movable encircle said elongated strap-like portions, such that they can be moved to a position behind the persons ears.

13. The device for protection of a person's eyes of claim 11, wherein each of said ear cushioning pads are formed by two strips of cushioning material which are secured to opposite sides of said elongated strap-like portions.

14. An eye protection device comprising:
    a first member formed of translucent material which encircles the wearer's head, said first member including a pair of enlarged portions for covering the eyes which are separated by a narrower bridging portion extending across the wearer's nose, and with a pair of elongated strap-like portions, one of which extends from each of said pair of enlarged portions for covering the eyes, p1 a cushioning material surrounding the outer periphery of the pair of enlarged portions for covering the eyes and the narrower nose bridging portion and secured to one side of said first member of translucent material for engaging a persons face, and
    a pair of complementary fastening means, one of said pair of complementary fastening means being provided on each of said elongated straps, said elongated straps being secured to each other by said complementary fastening means to retain said device over the eyes of a person.

15. The eye protection device of claim 14, wherein said cushioning material is a plastic foam.

16. The eye protection device of claim 15, wherein said plastic foam is of the open cell type.

17. The eye protection device of claim 15, wherein said plastic foam is of the closed cell type.

18. The eye protection device of claim 14, wherein said cushioning material is secured to said translucent material by an adhesive.

19. The eye protection device of claim 14, wherein said translucent material is formed of a polyester material.

20. The eye protection device of claim 14, wherein said translucent material is formed of Mylar®.

21. The eye protection device of claim 14, wherein said translucent material is formed of Teflon®.

22. The eye protection device of claim 14, wherein said translucent material is tinted.

23. The eye protection device of claim 14, wherein said cushioning material extends at varying distances from the translucent material, so as to maintain compressing contact with a person's face throughout its surface facing the person.

24. The eye protection device of claim 14, wherein an ear cushioning pad is provided on each of said elongated strap-like portions.

25. The eye protection device of claim 24, wherein said ear cushioning pads movable encircle said elongated strap-like portions, such that they can be moved to a position behind the person's ears.

26. The eye protection device of claim 24, wherein each of said ear cushioning pads are formed by two strips of cushioning material which are secured to opposite sides of said elongated strap-like portions.

* * * * *